United States Patent [19]

Englert et al.

[11] Patent Number: 4,999,371
[45] Date of Patent: Mar. 12, 1991

[54] SUBSTITUTED 3,4-DIHYDRO-2H-BENZOPYRANS, PROCESSES FOR THEIR PREPARATION, THEIR USE AND PHARMACEUTICAL PRODUCTS BASED ON THESE COMPOUNDS

[75] Inventors: Heinrich C. Englert; Hans-Jochen Lang, both of Hofheim am Taunus; Dieter Mania; Bernward Schölkens, both of Kelkheim, all of Fed. Rep. of Germany

[73] Assignee: Hoechst Aktiengesellschaft, Frankfurt am Main, Fed. Rep. of Germany

[21] Appl. No.: 151,584

[22] Filed: Feb. 2, 1988

[30] Foreign Application Priority Data

Feb. 4, 1987 [DE] Fed. Rep. of Germany ....... 3703227

[51] Int. Cl.$^5$ .................. C07D 405/04; A61K 31/40; A61K 31/435; A61K 31/55
[52] U.S. Cl. .................................... 514/422; 514/212; 514/337; 540/524; 546/136; 548/525
[58] Field of Search ........................ 548/525; 546/196; 514/212, 337, 422; 540/524

[56] References Cited

U.S. PATENT DOCUMENTS

| | | |
|---|---|---|
| 4,251,537 | 2/1981 | Evans . |
| 4,363,811 | 12/1982 | Evans . |
| 4,446,113 | 5/1984 | Evans . |
| 4,782,083 | 11/1988 | Cassidy .............................. 548/525 |

OTHER PUBLICATIONS

Pine, Organic Chemistry, 4th Ed., pp. 208-209.

Primary Examiner—Robert A. Wax
Assistant Examiner—F. Tsung
Attorney, Agent, or Firm—Finnegan, Henderson, Farabow, Garrett, and Dunner

[57] ABSTRACT

3,4-Dihydro-2H-benzo[b]pyrans of the formula I

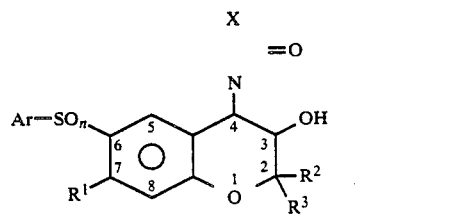

are described, in which
$R^1$ is H, OH, ($C_1$-$C_2$)-alkoxy, ($C_1$-$C_2$)-alkyl or $NR^4R^5$,
$R^4$ and $R^5$ being identical or different and representing H, ($C_1$-$C_2$)-alkyl or ($C_1$-$C_3$)-alkylcarbonyl,
$R^2$ and $R^3$ are identical or different and are alkyl having 1-4 carbon atoms,
Ar is an aromatic or heteroaromatic system which is unsubstituted or substituted,
n is 1 or 2 and
X is a $(CH_2)_r$ chain which can be interrupted by a heteroatom O, S or $NR^6$, $R^6$ being H or ($C_1$-$C_4$)-alkyl and
r being one of the numbers 2, 3, 4 or 5.

Processes for the preparation of these compounds, their use and pharmaceutical products based on these compounds are also described.

9 Claims, No Drawings

SUBSTITUTED 3,4-DIHYDRO-2H-BENZOPYRANS, PROCESSES FOR THEIR PREPARATION, THEIR USE AND PHARMACEUTICAL PRODUCTS BASED ON THESE COMPOUNDS

The invention relates to 3,4-dihydro-2H-benzo[b]pyrans of the formula I

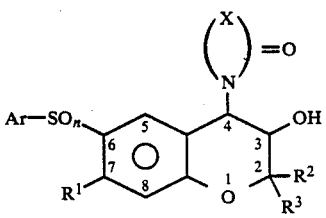

in which
- $R^1$ is H, OH, ($C_1$-$C_2$)-alkoxy, ($C_1$-$C_2$)-alkyl or $NR^4R^5$, $R^4$ and $R^5$ being identical or different and representing H, ($C_1$-$C_2$)-alkyl or ($C_1$-$C_3$)-alkylcarbonyl,
- $R^2$ and $R^3$ are identical or different and are alkyl having 1-4 carbon atoms,
- Ar is an aromatic or heteroaromatic system which is unsubstituted or substituted by 1 to 3 identical or different radicals ($C_1$-$C_2$)-alkyl, ($C_1$-$C_2$)-alkoxy, halogen, trifluoromethyl, CN, $NO_2$, CO-($C_1$-$C_2$)-alkyl or $SO_m$-($C_1$-$C_2$)-alkyl with m=1 or 2,
- n is 1 or 2, and
- X is a $(CH_2)_r$ chain which can be interrupted by a heteroatom O, S or $NR^6$, $R^6$ being H or ($C_1$-$C_4$)-alkyl and r being the numbers 2, 3, 4 or 5.

An aromatic system Ar is understood as meaning preferably phenyl, naphthyl or biphenylyl, and a 5-membered or 6-membered heteroaromatic system Ar is preferably a radical of a 5-membered or 6-membered O, N and/or S heterocyclic ring, in particular furyl, thienyl, isothiazolyl, oxazolyl, isoxazolyl, pyrazolyl, imidazolyl, thiazolyl, pyridyl, pyrazinyl, pyrimidinyl, pyridazinyl or triazinyl.

Halogen is to be understood as F, Cl, Br or I, preferably F, Cl and Br.

The carbon atoms 3 and 4 of the 3,4-dihydro-2H-benzo[b]pyran system (also abbreviated to "chroman system" below) of the formula I are asymmetrically substituted. The invention here relates only to those compounds which show opposite configurations at these centers, i.e. a "trans" -orientation of the substituents on these carbon atoms. If one of the substituents $R^1$,Ar-$SO_n$, $R^2$ and/or $R^3$ contains asymmetric centers or, if $R^2$ and $R^3$ are not identical (and thus generate an asymmetric carbon atom), compounds with both S-configured and R-configured centers are subjects of the invention.

The compounds may be in the form of optical isomers, of diastereoisomers, of racemates or of mixtures thereof.

Those compounds of the formula I are preferred in which $R^1$ to $R^3$ and $ArSO_n$ are as defined above, but X is a $(CH_2)_r$ chain with r=3 or 4.

Those compounds are particularly preferred in which $R^1$ to $R^3$ are as defined above, Ar is phenyl which is unsubstituted or substituted as defined above, n is 2 and X is a $(CH_2)_r$ chain with r=3 or 4.

Those compounds are especially preferred in which $R^1$ is H or ($C_1$-$C_2$)-alkoxy, $R^2$ and $R^3$ are as defined above, Ar is phenyl which is unsubstituted or monosubstituted by ($C_1$-$C_2$)-alkyl, cyano, ($C_1$-$C_2$)-alkoxy or halogen, n is 2 and X is a $(CH_2)_r$ chain with r=3 or 4.

Compounds which are structurally very closely related to the compounds according to the invention have been described in J. Med. Chem. 1986, 29, 2194–2201. They are summarized in that publication under the following general formula:

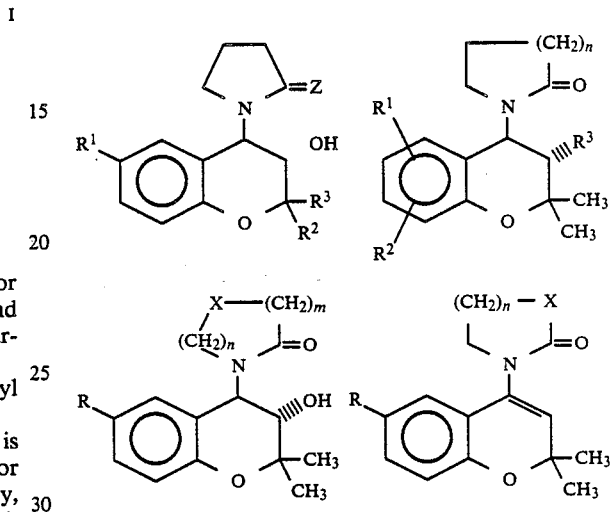

with $R^1$, $R^2$, $R^3$, Z, n, m and R being as defined therein. Many of these compounds also formed the subject of various patent applications, of which EP 0,107,423, EP 0,120,427, EP 0,076,075 and EP 0,120,428 should be mentioned here.

In particular, the compounds which are described as being particularly active in the reference cited above are those which have a CN or an $NO_2$ group in the 6-position of the 3,4-dihydro-2H-benzopyran system, particular importance attaching to (±)-6-cyano-3,4-dihydro-2,2-dimethyl-trans-4-(2-oxo-1-pyrrolidinyl)-2H-benzo[b]pyran-3ol, in particular. Compounds which have in the abovementioned 6-position sulfonylalkyl radicals or sulfoxyalkyl radicals are contained in the claims of the abovementioned patent applications but have not hitherto been obtained, and thus their activity has not been investigated either.

In a further patent specification (EP 0,173,848), the use of these compounds was described as appropriate also for other cardiovascular diseases. Particularly in the case of cardiac insufficiency or angina pectoris, a relaxing action on the vascular system can be of great therapeutic benefit. The experiments, reported in EP 0,173,848, on isolated vessels indicate such an effect of the compounds.

With the compounds I according to the invention a novel class of substances having an advantageous effect on the cardiovascular system has now been found. Surprisingly, the combination of an aryl radical Ar with a sulfonyl or sulfoxy group as substituent for the 6-position of the chroman system results in improved active properties. The observed superiority may relate to the potency in respect of lowering the blood pressure and/or relaxing certain vascular systems such as, for example, the thoracic aorta or the coronary system. Furthermore, it has been observed, in the model of the Langendorff heart, that in many cases the effect on the coronary blood flow is far more long-lasting than is the case with the abovementioned known compounds. As a result, compounds I are valuable therapeutic agents which are suitable for the treatment of high blood pressure and for the therapy of angina pectoris and cardiac insufficiency. Since these diseases may also occur in combination with one another, additional importance attaches to the compounds I.

The invention also relates to a process for preparing the compounds I, which comprises (a) reacting compounds of the formula II

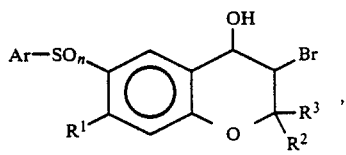

in which $R^1$ to $R^3$ and $ArSO_n$ are as defined above, with lactams of the formula III

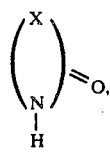

(b) reacting compounds of the formula IV

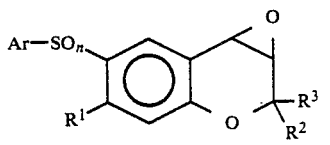

in which $R^1$ to $R^3$ and $ArSO_n$ are as defined above, with the lactams of the formula III

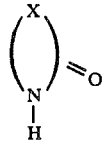

(c) acylating compounds of the formula V

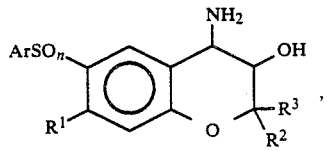

in which $R^1$ to $R^3$ and $ArSO_n$ are as defined above, to give the compounds VI

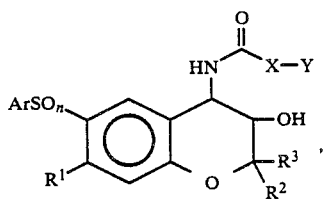

in which Y is a leaving group, such as chlorine or bromine, and $R^1$ to $R^3$ and $ArSO_n$ are as defined above, and cyclizing these compounds to give the compounds I, or (d) oxidizing compounds of the formula VII

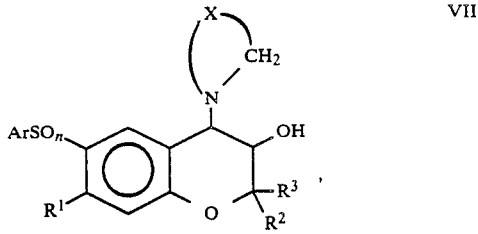

in which $R^1$ to $R^3$ and $ArSO_n$ are as defined above, to give the compounds I.

In the preparation of the compounds I by the methods (a) or (b), this is effected by reacting the compounds II or IV in a suitable solvent, preferably in dipolar aprotic solvents such as dimethyl sulfoxide or THF, with the lactams III, preferably under the action of bases, such as sodium hydride, K tert.-butylate or the like, which are known to be bases suitable for N-alkylations of lactams. The reaction temperature can here be varied within a wide range; preferably it is between 0° and room temperature or just above room temperature.

Lactams of the formula III are known in many cases, or they can readily be prepared by methods known from the literature. The compounds II or IV are novel. They can be prepared, for example, by the following synthesis route:

Compounds of the formula VIII

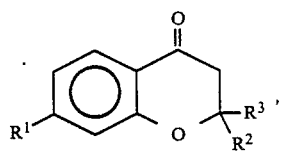

in which $R^1$, $R^2$ and $R^3$ are as defined above, are reacted with acid chlorides $Ar-SO_n-Cl$ in a manner known per se, analogously to the Friedel-Crafts acylation, to give compounds of the formula IX

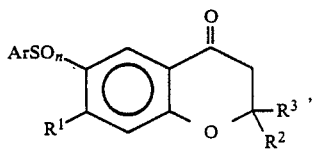

in which $R^1$, $R^2$, $R^3$, Ar and n are as defined above. By reductions under standard conditions, for example by means of $NaBH_4$ in methanol, these compounds are converted to the compounds X

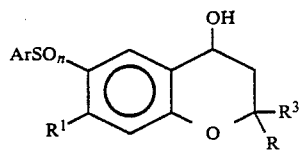

and then subjected to dehydration, for example by means of pyridine/phosphorus oxychloride, compounds of the formula XI

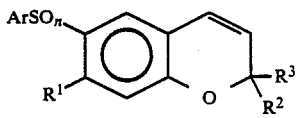   XI being formed.

Compounds XI can then readily be converted to the epoxides IV or the bromohydrins II by standard methods.

If $R^1$ in this reaction sequence is $NH_2$ or OH, protective groups such as the dimethylaminomethylene group for $NH_2$ or the acetyl or methyl groups for the OH group may be necessary. These are eliminated again by conventional methods at suitable stages, preferably after the reactions described in processes (a) or (b) have been carried out.

Chromenes of the formula XI are prepared in some cases by a thermally induced cyclization of the corresponding propargyl ethers XII

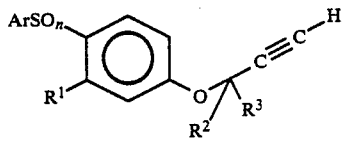   XII in a manner known per se. These can in turn be prepared in a manner known per se from the phenols XIII and the propargyl chlorides XIV.

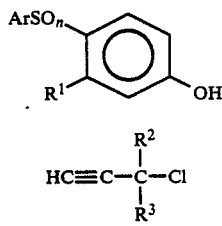   XIII

XIV

Processes (c) and (d) can be used particularly advantageously when enantiomerically pure final products I are desired. Compounds V and VII are, in contrast to compounds I, basic and thus are able to form salts with organic acids. They can be obtained in an enantiomerically pure form in a manner known per se by crystallization using a suitable optically pure acid such as, for example, (+)-mandelic acid or (+)-lactic acid, and converted by processes (c) and (d) into enantiomerically pure final products I.

Enantiomerically pure final products I can, however, also be resolved from racemic final products I by familiar methods of racemate resolution such as, for example, chromatographic separation using chiral phases or derivatization of the racemic products using optically pure acid derivatives (ester formation via the 3-hydroxy group of the chroman system) or using optically pure isocyanates (carbamate formation via the 3-hydroxy group). The diastereomeric isocyanates or esters obtained in this way can be separated by familiar methods (crystallization or chromatography) and converted into the optically pure final compounds I with elimination of the optically active auxiliary group on the 3-OH group. Separation of the diastereomeric 3-methoxyacetates has proved particularly advantageous in this connection.

As already mentioned, the compounds I according to the invention can be used as antihypertensive agents, as coronary therapeutics or as agents for the treatment of cardiac insufficiency They can be used both in human and veterinary medicine for these purposes They are administered enterally, for example orally, or parenterally (such as by injection into the vascular system, for example intravenously), in dosages of at least 0.002 mg/kg/day, preferably at least 0.01 mg/kg/day and especially at least 0.1 mg/kg/day, up to at most 20 mg/kg/day, preferably up to 10 mg/kg/day and especially up to 4 mg/kg/day, in capsules, coated pills, tablets, powders, suppositories or solutions with or without additions of formulating auxiliaries. These data relate to an adult human of 75 kg body weight. The compounds I are suitable for the treatment of cardiovascular diseases, such as hypertension, angina pectoris or cardiac insufficiency, alone or in combination with other medicaments acting on the cardiovascular system, such as diuretics, Ca antagonists, ACE inhibitors or β-sympathicolytics.

The compounds of the formula I, listed in the table which follows, can be obtained, for example, according to the invention:

(1) 2,2-dimethyl-3,4-dihydro-7-methoxy-6-(p-chlorophenyl-sulfonyl)-trans-4-(2-oxo-1-pyrrolidinyl)-2H-benzo[b]-pyran-3-ol, (2) 2,2-dimethyl-3,4-dihydro-6-(p-chlorophenylsulfonyl)-trans-4-(2-oxo-1-piperidinyl)-2H -benzo[b]pyran-3ol, (3) 2,2-dimethyl-3,4-dihydro-6-(p-nitrophenylsulfonyl)-trans-4(2-oxo-1-pyrrolidinyl)-2H -benzo[b]pyran-3-ol, (4) 2,2-dimethyl-3,4-dihydro-6-(p-cyanophenylsulfonyl)-trans-4-(2-oxo-1-pyrrolidinyl)-2H -benzo[b pyran-3-ol, (5) 2,2-dimethyl-3,4-dihydro-6-(p-methoxyphenylsulfonyl)-trans-4-(2-oxo-1-pyrrolidinyl)-2H -benzo[b]pyran-3-ol, (6) 2,2-dimethyl-3,4-dihydro-6-(p-trifluoromethylphenyl -sulfonyl)-trans-4-(2-oxo-1-pyrrolidinyl)-2H-benzo[b]-pyran-3-ol, (7) 2,2-dimethyl-3,4-dihydro-6-(p-methylsulfonylphenyl)-sulfonyl-trans-4-(2-oxo-1-pyrrolidinyl) -2H-benzo[b]-pyran-3-ol, (8) 2,2-dimethyl-3,4-dihydro-6-(p-acetylphenylsulfonyl)-trans-4-(2-oxo-1-pyrrolidinyl)-2H -benzo[b]pyran-3-ol, (9) 2,2-dimethyl-3,4-dihydro-7-methylamino-6-phenylsulfonyl-trans-2(2-oxo-1-pyrrolidinyl) -2H-benzo[b]-pyran-3-ol,

(10) 2,2-dimethyl-3,4-dihydro-7-fluoro-6-phenylsulfonyl-trans-(2-oxo-1-pyrrolidinyl)-2H -benzo[b]pyran-3-ol,

(11) 2,2-diethyl-3,4-dihydro-7-fluoro-6-phenylsulfonyl-trans-(2-oxo-1-pyrrolidinyl)-2H -benzo[b]pyran-3-ol,

(12) 2,2) 2,2-dimethyl-7-chloro-3,4-dihydro-6-phenylsulfonyl-trans-(2-oxo-1-pyrrolidinyl) -2H-benzo[b]-pyran-3-ol,

(13) 2,2-dimethyl-3,4-dihydro-6-(4-chloro-3-methylphenyl-sulfonyl)-trans-(2-oxo-1-pyrrolidinyl)-2H-benzo[b]pyran-3-ol,

(14) 2,2-dimethyl-3,4-dihydro-6-(4-chlorophenylsulfonyl)-trans-(5-oxo-3-thiazolidinyl)-2H -benzo[b]pyran-3-ol,

(15) 2,2-dimethyl-3,4-dihydro-trans-4-(4-methyl-2-oxo-1-piperazinyl)-6-phenylsulfonyl-2H-benzo[b]pyran-3-ol,
(16) 2,2-dimethyl-3,4-dihydro-6-phenylsulfonyl-trans-4(2-oxo-1-morpholinyl)-2H-benzo[b]pyran-3-ol,
(17) 2,2-dimethyl-3,4-dihydro-6-phenylsulfonyl-trans-4-(5-oxo-3-oxazolinyl)-2H-benzo[b]pyran-3-ol,
(18) 3,4-Dihydro-2,2-dimethyl-6-(p-fluorophenylsulfonyl)-trans-4-(2-oxo-1-pyrrolidinyl)-2H -benzo[b]pyran-3-ol,
(19) 3,4-Dihydro-2,2-dimethyl-6-(o-fluorophenylsulfonyl)-trans-4-(2-oxo-1-pyrrolidinyl)-2H -benzo[b]pyran-3-ol,
(20) 3,4-Dihydro-2,2-dimethyl-6-(3-pyridylsulfonyl)-trans-4-(2-oxo-1-pyrrolidinyl)-2H -benzo[b]pyran-3ol,
(21) 3,4-Dihydro-2,2-dimethyl-6-(2-pyrimidinylsulfonyl)-trans-4-(2-oxo-1-pyrrolidinyl)-2 H-benzo[b]pyran-3ol,
(22) 3,4-Dihydro-2,2-dimethyl-6-(2-furylsulfonyl)-trans-4-(2-oxo-1-pyrrolidinyl)-2H -benzo[b]pyran-3-ol.

EXAMPLE 1

3,4-Dihydro-2,2-dimethyl-7-methoxy-6-(p-tolylsulfonyl)-trans-4-(2-oxo-1-pyrrolidinyl)-2H -benzo[b]-3-ol.

4.3 g (0.0097 mol) of 3-bromo-3,4-dihydro-2,2-dimethyl-7-methoxy-6-(p-tolylsulfonyl)-2H -benzo[b]-pyran-4-ol are dissolved in 28 ml of dimethyl sulfoxide, 3.5 ml of 2-pyrrolidinone (0.0465 mol) and 0.78 g of sodium hydride (80 % suspension in oil) (0.0325 mol) are added and the mixture is stirred for 3 hours at 40° C. and left to stand overnight, poured on ice water and filtered with suction. The precipitate is recrystallized from isopropanol: white crystals of melting point 263–65° C.

Preparation of the starting compound:
3-Bromo-3,4-dihydro-2,2-dimethyl-7-methoxy-6-(p-tolyl-sulfonyl)-2H-benzo[b]pyran-4-ol is obtained from 2,2-di-methyl-7-methoxy-6-(p-tolylsulfonyl)-2H-chromene and N-bromosuccinimide in a 9:1 dimethyl sulfoxide/H2O mixture. Melting point: 200–201° C.

2,2-Dimethyl-7-methoxy-6-(p-tolylsulfonyl)-2H-chromene is obtained from 2,2-dimethyl-7-methoxy-6-(p-tolylsulfonyl)-chroman-4-ol with phosphorus oxychloride/pyridine in benzene. Melting point: 132–33° C.

2,2-Dimethyl-7-methoxy-6-(p-tolylsulfonyl)-chroman-4-ol is obtained from 2,2-dimethyl-7-methoxy-6-(p-tolylsulfonyl)-chroman-4-one with NaBH4 in ethanol. Melting point: 196–97° C.

2,2-Dimethyl-7-methoxy-6-(p-tolylsulfonyl)-chroman-4-one is obtained from 2,2-dimethyl-7-methoxychroman-4-one and p-toluenesulfonic acid chloride in the presence of aluminum chloride in methylene chloride. Melting point: 221–23° C.

EXAMPLE 2

3,4-Dihydro-2,2-dimethyl-7-methoxy-6-(p-tolylsulfonyl)-trans-4-(2-oxo-1-piperidinyl)-2H -benzo[b]pyran-3-ol.

5 g (0.011 mol) of 3-bromo-3,4-dihydro-2,2-dimethyl-7-methoxy-6-(p-tolylsulfonyl)-2H-benzo [b]pyran-4ol are dissolved in 32 ml of dimethyl sulfoxide, 4.9 g of valerolactam (0.0526 mol) and 0.8 g (0.033 mol) of NaH, 80 % suspension in oil, are added and the mixture is stirred for 5 hours at 40° C., poured on ice water and filtered with suction. The residue is boiled up several times with methanol. White crystals of melting point 261–63° C.

EXAMPLE 3

3,4-Dihydro-2,2-dimethyl7-methoxy-6-phenylsulfonyl-trans-4-(2-oxo-1-pyrrolidinyl)-2H -benzo[b]-3-ol The compound is prepared analogously to Example 1 from 3-bromo-3,4-dihydro-2,2-dimethyl-7-methoxy-6-phenylsulfonyl-2H-benzo[b]pyran-4-ol. White crystals of melting point 227–29° C.

Separation of the antipodes, Example 3a
1.075 g (0.0025 mol) of (+)-3,4-dihydro-2,2-dimethyl-7-methoxy-6-phenylsulfonyl-trans-4-(2-oxo-1-pyrrolidinyl)-2H-benzo[b]pyran-3-ol are dissolved in 5 ml of 1,2-dichlorobenzene, 0.9 g of S(-)-1-phenylethyl isocyanate is added, and the mixture is stirred at 140° C. for about 12 h. The complete mixture is then chromatographed on silica gel using the solvent system toluene-/ethyl acetate 1:1. The slower migrating diastereomeric carbamate can be enriched and can be obtained pure by crystallization from toluene (melting point 243–245° C.). Hydrolysis with NaOH in EtOH at 80° C. results in (+)-3,4-dihydro-2,2-dimethyl-7-methoxy-6-phenylsulfonyl-trans-4-(2-oxo -1-pyrrolidinyl)-2H-benzo[b]pyran-3-ol of melting point 209–211° C. and $[\alpha]_D = +109°$ (c=0.28; CHCl3)

Preparation of the starting material:
3-Bromo-3,4-dihydro-2,2-dimethyl-7-methoxy-6-phenylsulfonyl-2H-benzo[b]pyran-4-ol is obtained from 2,2-dimethyl-7methoxy-6phenylsulfonyl-2H-chromene and N-bromosuccinimide in a 9:1 dimethyl sulfoxide/H2O mixture. Melting point: 202–203° C.

2,2-Dimethyl-7-methoxy-6-phenylsulfonyl-2H-chromene is obtained from 2,2-dimethyl-4-hydroxy-7-methoxy-6-phenyl-sulfonyl-chromene with pyridine/phosphorus oxychloride in benzene. Melting point: 140–41° C.

2,2-Dimethyl-4-hydroxy-7-methoxy-6-phenylsulfonylchroman is obtained from 2,2-dimethyl-7-methoxy-6-phenylsulfonyl-chromene-4-one with sodium borohydride in methanol. Melting point: 146–147° C.

2,2-Dimethyl-7-methoxy-6-phenylsulfonylchroman-4-one is obtained from phenylsulfonyl chloride, 2,2-dimethyl-7-methoxychroman-4-one and aluminum chloride in methylene chloride. Melting point: 223–25° C.

EXAMPLE 4

3,4-Dihydro-2,2-dimethyl-6-(4-methylphenylsulfonyl)-trans-4-(2-oxo-1-pyrrolidinyl)-2H -benzo[b]pyran-3-ol 0.75 g (0.025 mol) of 80 % NaH is introduced into 8.2 g (0.02 mol) of 3-bromo-3,4-dihydro-2,2-dimethyl-6-(4'-methyl-phenylsulfonyl)-2H-benzo[b]pyran -4-ol in 30 ml of dimethyl of dimethyl sulfoxide. After stirring for one hour at 20°, a further 0.75 g (0.025 mol) of 80 % NaH and 1.9 ml (0.025 mol) of 2-pyrrolidone are added and the mixture is stirred for 45 minutes at 40° and for 6 hours at 20°. After the mixture has been introduced into ice water, the precipitate is filtered off with suction, dried and recrystallized several times from methanol. Crystals of melting point: 242–243°.

Preparation of the starting material

3-Bromo-3,4-dihydro-2,2-dimethyl-6-(4-methylphenyl-
sulfonyl)-2H-benzo[b]pyran-4-ol
2H-benzo[b]pyran-4-ol 14.2 g (0.08 mol) of freshly recrystallized N-bromosuccinimide are introduced with cooling (isopropanol/dry ice) at about 15° C. into 12.6 g (0.04 mol) of 2,2-dimethyl-6-(4'-methylphenylsulfonyl)-chromene in a solution of 70 ml of dimethyl sulfoxide and 1.4 ml of water. The temperature rises temporarily to 27° C. The mixture is cooled to 20° C. and, after stirring for 1 hour, introduced into ice/ethyl acetate. The ethyl acetate phase is washed several times with water and dried over $Na_2SO_4$. On concentrating, the bromohydrin derivative crystallizes. Crystals of melting point: 141–142° C.

EXAMPLE 5

3,4-Dihydro-2,2-dimethyl-6-phenylsulfonyl-trans-4-(2-oxo1-pyrrolidinyl)-2H-benzo[b]pyran-3-ol A solution of 6.3 g (0.02 mole) of 3,4-dihydro-2,2-dimethyl-3,4-epoxy-6-phenylsulfonyl-2H-benzo [b]pyran in 20 ml of DMSO is added dropwise at 20° to a suspension of 0.6 g (0.02 mole) of 80% NaH in 10 ml DMSO. Then 2.3 ml (0.03 mole) of 2-pyrrolidinone are added, and the mixture is stirred at 45°) for 1 hour. After it has stood at 20° overnight, it is introduced into ice-water. The precipitate is filtered off with suction, washed to neutrality, dried and chromatographed on silica gel using methylene chloride/methanol 19:1. 30 ml fractions are collected. Fractions 12–25 are concentrated, and the residue is recrystallized from acetonitrile. Melting point: 201–202°

Preparation of the starting material:
3,4-Dihydro-2,2-dimethyl-3,4-epoxy-6-phenylsulfonyl-2H-benzo [b]pyran is obtained from 3-bromo-3,4-dihydro-2,2-dimethyl-6-phenylsulfonyl-2H-benzo[b]pyran-4-ol using NaH in DMSO. Melting point: 103–105°

3-Bromo-3,4-dihydro-2,2-dimethyl-6-phenylsulfonyl-2H-benzo [b pyran-4-ol is obtained from 2,2-dimethyl-6-phenyl-sulfonyl-2H-chromene and N-bromosuccinimide in a 9:1 dimethyl sulfoxide/$H_2O$ mixture. Melting point: 126°

2,2-Dimethyl-6-phenylsulfonyl-2H-chromene, with melting point 70–71°, was obtained by known methods from 6phenylsulfonylphenyl 1,1-dimethylpropargyl ether. This ether was obtained, likewise in a known manner, from 6-phenylsulfonylphenol and 3-methyl-3-chlorobutyne.

(+)-3,4-Dihydro-2,2-dimethyl-6-phenylsulfonyl-4-(2-oxo-1-pyrrolidinyl)-2H-benzo[b]pyran -3-ol (Example 5a)

(±)-3-,4-Dihydro-2,2-dimethyl-6-phenylsulfonyl-4-(2-oxo-1-pyrrolidinyl)-2H-benzo[b]pyran-3ol is esterified with (−)-menthoxyacetyl chloride by standard methods. The diastereomeric esters are separated on a silica gel column using methylene chloride/ethyl acetate (9:1) and hydrolyzed with alcoholic sodium ethylate solution at 20°, with stirring. After dilution with cold water, the precipitate is filtered off with suction and washed to neutrality, and is triturated with ether.

(+)-3,4-Dihydro-2,2-dimethyl-6-phenylsulfonyl-4-(2-oxo-1-pyrrolidinyl)-2H-benzo[b]pyran -3-ol Melting point: 122–123°, $[\alpha]_D = +39.5°$ (c−1, ethanol)

EXAMPLE 6

6-(4-Chlorophenylsulfonyl)-3,4-dihydro-2,2-dimethyl-7-methoxy-trans-4-(2-oxo-1-pyrrolidinyl )-2H-benzo[b]pyran-3-ol 5 The compound is prepared in analogy to Example 1 from 3-bromo-6-(4-chlorophenylsulfonyl)-3,4-dihydro-2,2-di-methyl-7-methoxy-2H-benzo[b]pyran-4-ol. White crystals of melting point 260–262° C.

Preparation of the starting compounds:
In analogy to Example 1: 3-Bromo-6-(4-chlorophenylsulfonyl)-3,4-dihydro-2,2-di-methyl-7-methoxy-2H-benzo[b]pyran-4-ol of melting point 175–177° C.
6-(4-Chlorophenylsulfonyl)-2,2-dimethyl-7-methoxy-chromene of melting point 142–143° C.

EXAMPLE 7

6-(4-Bromophenylsulfonyl)-3,4-dihydro-2,2-dimethyl-7-methoxy-trans-4-(2-oxo-1-pyrrolidinyl) -2H-benzo[b]pyran-3-ol In analogy to Example 1 from 3-bromo-6-(4-bromophenylsulfonyl)-3,4-dihydro-2,2-dimethyl-7-methoxy -2H-benzo[b]-pyran-4-ol White crystals of melting point 281–282° C.

EXAMPLE 8

3,4-Dihydro-2,2-dimethyl-7-methoxy-6-(4-methoxyphenylsulfonyl)-trans-4-(2-oxo-1-pyrrolidinyl)-2H-benzo[b]-pyran-3-ol The compound is prepared in analogy to Example 1 from 3-bromo-3,4-dihydro-2,2-dimethyl-7-methoxy-6-(4-methoxy-phenylsulfonyl)-2H-benzo[b]pyran-4-ol and has a melting point of 286–287° C.

EXAMPLE 9

3,4-Dihydro-2,2-dimethyl-7-methoxy-6-(2-thienylsulfonyl)-trans-4-(2-oxo-1-pyrrolidinyl) --2H-benzo[b pyran-3-ol In analogy to Example 1 from 3-bromo-3,4-dihydro-2,2-dimethyl-7-methoxy-6-(2-thienylsulfonyl) -2H-benzo[b]pyran-4-ol, melting point: 135–136° C.

EXAMPLE 10

3,4-Dihydro-2,2-dimethyl-7-ethoxy-6-phenylsulfonyl-trans-4-(2-oxo-1-pyrrolidinyl)-2H-benzo [b]pyran-4-ol, In analogy to Example 1from 3-bromo-3,4-dihydro-2,2-dimethyl-7-ethoxy-6-phenylsulfonyl-2H-benzo [b]pyran-4-ol, melting point: 197–198° C.

EXAMPLE 11

3,4-Dihydro-2,2-dimethyl-7-methoxy-6-phenylsulfonyl-trans-4-(2-oxo-1-piperidinyl)-2H-benzo [b]pyran-3ol In analogy to Example 2 from 3-bromo-3,4-dihydro-2,2-dimethyl-7-methoxy-6-phenylsulfonyl-2H-benzo [b]pyran-4-ol.
White crystals of melting point 157–158° C.

EXAMPLE 12

6-(4-Cyanophenylsulfonyl)-3,4-dihydro-2,2-dimethyl-trans-4-(2-oxo-1-pyrrolidinyl)-2H-benzo [b]pyran-3-ol In analogy to Example 1 from 3-bromo-6-(4-cyanophenylsulfonyl)-3,4-dihydro-2,2-dimethyl-2H-benzo [b]pyran-4-ol. White crystals of melting point 234–235° C.

Preparation of the starting material:

3-Bromo-6-(4-cyanophenylsulfonyl)-3,4-dihydro-2,2-di-methyl-2H-benzo[b]pyran-4-ol is obtained as described under Example 3 from 6-(4-cyanophenylsulfonyl)-2,2-dimethyl-3 chromene. Melting point: 157–158° C.

EXAMPLE 13

3,4-Dihydro-2,2-dimethyl-6-(2-methoxyphenylsulfonyl)-trans-4-(2-oxo-1-pyrrolidinyl)-2H-benzo[b]pyran-3-ol In analogy to Example 1 from 3-bromo-3,4-dihydro-2,2-dimethyl-6-(2-methoxyphenylsulfonyl)-2H-benzo[b]pyran-3-ol. White crystal of melting point 196–198° C.

EXAMPLE 14

3,4-Dihydro-2,2-dimethyl-6-(2-methylphenylsulfonyl)-trans4-(2-oxo-1-pyrrolidinyl)-2H-benzo [b]pyran-3-ol In analogy to Example 1. White crystals of melting point 214–216° C.

EXAMPLE 15

3,4-Dihydro-2,2-dimethyl-6-(2-chlorophenylsulfonyl)-trans4-(2-oxo-1-pyrrolidinyl)-2H-benzo [b]pyran-3-ol In analogy to Example 1. White crystals of melting point 85–87° C.

EXAMPLE 16

Preparation of 3,4-dihydro-2,2-dimethyl-6-phenylsulfonyl-trans-4-(2-oxo-1-pyrrolidinyl)-2H-benzo [b]pyran-3-ol (compound from Example 5 by process variant c)

A solution of 3-bromo-3,4-dihydro-2,2-dimethyl-6-phenyl-sulfonyl-2H-benzo[b]pyran-4-ol in ethanol is shaken under a pressure of 8 bar of $NH_3$ in an autoclave at 50° for 8 hours. After cooling, the mixture is concentrated to dryness, and the residue is recrystallized from ethyl acetate. 4-Amino-3,4-dihydro-2,2-dimethyl-6-phenylsulfonyl-2H-benzo[b]pyran-3-ol of melting point 160–163° C. is obtained and is immediately subjected to acetylation with 5-chlorobutyryl chloride. For this purpose, the substance and the acid chloride in $CH_2Cl_2$ and in a two-phase mixture with 2 N sodium hydroxide solution are stirred at room temperature for 24 hours. After customary working up, 4-(5-chlorobutyrylamino)-3,4-dihydro-2,2-dimethyl-6-phenylsulfonyl-2H-benzo[b]pyran-4-of melting point 155–157° C. is obtained. Cyclization to give the title compound is carried out by dissolving the substance in tetrahydrofuran, adding a stoichiometric amount of 80% NaH suspension in oil, and stirring the mixture at room temperature for 24 hours. The final product is identical to the product obtained by process (b). Melting point: 200–201°. If 4-amino-3,4-dihydro-2,2-dimethyl-6-phenyl-sulfonyl-2H-benzo[b]pyran-3-ol is subjected to racemate resolution, it is possible to obtain from its (+)-enantiomer the pure (+)-enantiomer from Example 5a with the data indicated there.

EXAMPLE 17

3,4-Dihydro-2,2-dimethyl-6-phenylsulfoxy-trans-4-(2-oxo-1-pyrrolidinyl)-2H-benzo[b]pyran -3-ol In analogy to Example 1. Melting point: 211–212° C.

Pharmalogical Data

Coronary flow in the Langendorff heart preparation of Guinea pigs (a) Method

Guinea pigs of either sex were killed by a blow on the head. The hearts were quickly removed and perfused according to Langendorff (Langendorff, Pflügers Arch. Ges. Physiol. 190, 280 (1895)) with a Ringer solution containing 154 mMol NaCl, 5,6 mMol KCl, 1,9 mMol $CaCl_2$, 2,4 mMol $NaHCO_3$ and 5 mMol glucose which was gassed with oxygen. The temperature of the solution was 37° C. The test substances dissolved in propanediol (0,1%) were added to the inflowing Ringer solution by bolus injection into the inflow tract. The effect, i.e. changes of the coronary outflow, was measured with a drop counter and registered on a Hellige Multiscriptor (Hellige GmbH, Freiburg, Germany) For each compound increase in coronary outflow was measured for three different doses and each dose was tested in 6 different heart preparations. From these data, $ED_{50}$ values were calculated (Probit-analysis and linear regression) indicating the dose responsible for a 50% increase of coronary outflow. Duration of elevated coronary outflow was measured for 6 heart preparations for a single dose as indicated in the following table.

| Compound | Results $ED_{50}$ | Duration (Dose) |
|---|---|---|
| (+)-3,4-Dihydro-2,2-dimethyl-6-phenylsulfonyl-trans-4-(2-oxo-1-pyrrolidinyl)-2H-benzo[b]pyran-3-ol example 5a | 100 ng | 13 min (100 ng) |
| (±)-3,4-Dihydro-2,2-dimethyl-6-phenylsulfonyl-trans-4-(2-oxo-1-pyrrolidinyl)-2H-benzo[b]pyran-3-ol example 5 | 304 ng | 11 min (400 ng) |
| (±)-3,4-Dihydro-2,2-dimethyl-6-(2-methylphenylsulfonyl-trans-4-(2-oxo-1-pyrrolidinyl)-2H-benzo[b]pyran-3-ol example 14 | 180 ng | 13 min (200 ng) |
| (±)-3,4-Dihydro-2,2-dimethyl-7-methoxy-6-phenylsulfonyl-trans-4-(2-oxo-1-pyrrolidinyl)-2H-benzo[b]pyran-3-ol example 3 | 670 ng | 14 min (500 ng) |
| (±)-3,4-Dihydro-2,2-dimethyl-7-methoxy-6-phenylsulfonyl-trans-4-(2-oxo-1-pyrrolidinyl)-2H-benzo[b]pyran-3-ol example 3a | 370 ng | 11 min (500 ng) |
| (±)-3,4-Dihydro-2,2-dimethyl-trans-4-(2-oxo-1-pyrrolidinyl)-6-p-tolylsulfonyl-2H-benzo[b]-pyran-3-ol example 4 | 570 ng | 11 min (500 ng) |
| (±)-6-Cyano-3,4-dihydro-2,2-dimethyl-trans-4-(2-oxo-1-pyrrolidinyl)-2H-benzo[b]pyran-3-ol | 590 ng | 6 min (500 ng) |

| Compound | Results ED$_{50}$ | Duration (Dose) |
|---|---|---|
| (compound from J. Med. Chem. 1986, 29, 2194-2201) (±)-2,2-Dimethyl-3,4-dihydro-7-methoxy-6-methylsulfonyl-trans-4-(2-oxo-1-pyrrolidinyl)-2H-benzo[b]pyran-3-ol according to EP 173 848 | >100 μg | — |
| (±)-2,2-Dimethyl-3,4-dihydro-6-methylsulfonyl-trans-4-(2-oxo-1-pyrrolidinyl)-2H-benzo[b]pyran-3-ol according to EP 173 848 | 2770 ng | 5 min (2000 ng) |

We claim:

1. A 3,4-dihydro-2-benzo[b]pyran of the formula I

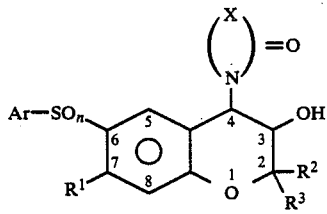

in which

R$^1$ is H, OH, (C$_1$-C$_2$)-alkoxy, (C$_1$-C$_2$)-alkyl or NR$^4$R$^5$, R$^4$ and R$^5$ being identical or different and representing H, (C$_1$-C$_2$)-alkyl or (C$_1$-C$_3$)-alkylcarbonyl, R$^2$ and R$^3$ are identical or different and are alkyl having 1-4 carbon atoms, Ar is phenyl which is unsubstituted or substituted by 1 to 3 identical or different radicals selected from the group consisting of (C$_1$-C$_2$)-alkyl, (C$_1$-C$_2$)-alkoxy, halogen, trifluoromethyl, CN, NO$_2$, CO-(C$_1$-C$_2$)-alkyl and SO$_m$-(C$_1$-C$_2$)-alkyl with m=1 or 2, n is 1 or 2 and X is a (CH$_2$)$_r$ chain and r being the numbers 3, 4 or 5.

2. A compound I as claimed in claim 1, wherein at least one of the substituents or indices has the following meaning:

Ar=phenyl, and
X=(CH$_2$)$_r$ with r=3 or 4.

3. A compound I as claimed in claim 1, wherein at least one of the substituents or indices has the following meaning:

Ar=phenyl which is unsubstituted or substituted as defined in claim 1, and
X=(CH$_2$)$_r$ with r=3 or 4.

4. A compound I as claimed in claim 1, wherein at least one of the substituents or indices has the following meaning:

R$^1$ =H or (C$_1$-C$_2$)-alkoxy,
Ar=phenyl which is unsubstituted or monosubstituted by (C$_1$-C$_2$)-alkyl, cyano, (C$_1$-C$_2$)-alkoxy or halogen,
n=2 and
X=(CH$_2$)$_r$ with r=3 or 4.

5. A compound I as claimed in claim 1, wherein at least one of the substituents or indices has the following meaning:

R$^1$=H or CH$_3$O
R$^2$=R$^3$=CH$_3$
Ar=phenyl
n=2
X =(CH$_2$)$_3$.

6. A method for treating cardiovascular disorders, which comprises administering an effective amount for said treatment of a compound I as claimed in claim 1 together with pharmaceutically suitable excipients.

7. A method for treating hypertension, angina pectoris or cardiac insufficiency in a mammal which comprises administering an effective amount for said treatment of a compound of the formula I as claimed in claim 1.

8. A pharmaceutical composition for the treatment of hypertension, angina pectoris or cardiac insufficiency which comprises an effective amount for said treatment of a compound I as claimed in claim 1 together with a pharmaceutically acceptable carrier.

9. The compound (+) −3,4-dihydro-2,2-dimethyl-6-phenylsulfonyl-4-(2-oxo-1-pyrrolidinyl)-2H -benzo[b]pyran-3-ol.

* * * * *